(12) United States Patent
Asou et al.

(10) Patent No.: US 8,039,253 B2
(45) Date of Patent: Oct. 18, 2011

(54) PHARMACEUTICAL FOR PREVENTION AND TREATMENT OF DEMYELINATING DISEASE

(75) Inventors: Hiroaki Asou, Tokyo (JP); Makoto Sugawa, Shizuoka (JP)

(73) Assignees: Tokyo Metropolitan Institute of Gerontology, Tokyo (JP); Chugai Seiyaku Kabushiki Kaisha, Tokyo (JP)

( * ) Notice: Subject to any disclaimer, the term of this patent is extended or adjusted under 35 U.S.C. 154(b) by 1803 days.

(21) Appl. No.: 10/312,721

(22) PCT Filed: Jun. 29, 2001

(86) PCT No.: PCT/JP01/05641
§ 371 (c)(1),
(2), (4) Date: Dec. 30, 2002

(87) PCT Pub. No.: WO02/02135
PCT Pub. Date: Jan. 10, 2002

(65) Prior Publication Data
US 2005/0032682 A1    Feb. 10, 2005

(30) Foreign Application Priority Data
Jun. 30, 2000 (JP) ................................ 2000-199421

(51) Int. Cl.
C12N 5/00 (2006.01)
C12N 5/02 (2006.01)
C12N 5/07 (2006.01)
C07K 14/00 (2006.01)

(52) U.S. Cl. ......... 435/325; 435/347; 435/377; 530/350

(58) Field of Classification Search ....................... None
See application file for complete search history.

(56) References Cited

U.S. PATENT DOCUMENTS 6,165,783 A * 12/2000 Weiss et al. .................... 435/325
7,410,941 B1 * 8/2008 Brines et al. ...................... 512/2

FOREIGN PATENT DOCUMENTS

| EP | 1 072 609 A2 | 1/2001 |
|---|---|---|
| JP | 5-246885 | 9/1993 |
| WO | WO 95/03821 * | 2/1995 |
| WO | WO 99/21966 A1 | 5/1999 |
| WO | WO 00/61164 A1 | 10/2000 |

OTHER PUBLICATIONS

Hart et al., Curr Opin Neurol 16: 375-383, 2003.*
Stuve et al, Curr Opin Neurol 16: 393-401, 2003.*
Cassan et al., J Neurochem 100: 883-892, 2007.*
Schmandt et al Drug Dis Today Disease Models 3: 349-358, 2006.*
Zhang et al., Br Res 1034: 34-39, 2005.*
Fontoura et a. Int Rev Immunol 24: 415-446, 2005.*
McFarland et al Nat Immunol 8: 913-919, 2007.*
Stengel et al. Prog Neurobiol 68: 361-376, 2002.*
Wells, 1990, Biochemistry 29:8509-8517.*
Ngo et al., 1994, The Protein Folding Problem and Tertiary Structure Prediction, pp. 492-495.*
Bork, 2000, Genome Research 10:398-400.*
Skolnick et al., 2000, Trends in Biotech. 18(1):34-39.*
Doerks et al., 1998, Trends in Genetics 14:248-250.*
Smith et al., 1997, Nature Biotechnology 15:1222-1223.*
Brenner, 1999, Trends in Genetics 15:132-133.*
Bork et al., 1996, Trends in Genetics 12:425-427.*
Stanislaus et al (Neurosc Lett 269: 71-74, 1999.*
Tanaka et al. Brain Res 989: 172-179, 2003.*
Zuccarello et al. Neurosc 144: 865-877, 2007.*
Gensert et al.Neuron 19: 197-203, 1997.*
Brines et al. PNAS 97: 10526-10531, 2000.*
Pendlebury et al. Mag Res Imag 18: 369-378, 2000.*
Tabira et al. (Int J Dev Neurosc 13: 241-252, 1995).*
Mancardi et al. J Neuroimmunol 107: 178-183, 2000.*
Al-Omaishi et al. J Leukoc Biol 65: 444-452, 1999.*
Bernaudin, et al, "A Potential Role for Erythropoietin in Focal Permanent Cerebral Ischemia in Mice", Journal of Cerebral Blood flow and Metabolism. 19:643-651. 1999.
Koshimura, et al, "Effects of Erythropoietin on Neuronal Activity", Journal Neurochemistry. 72(6):2565-2572. 1999.
Masuda, et al, "In vitro neuroprotective action of recombinant rat erythropoietin produced by astrocyte cell lines nd comparative studies with erythropoietin produced by Chinese hamster ovary cells". Cytotechnology, 29:207-213. 1999.
Sasaki, et al, "Novel physiological functions of erythropoietin an its biosynethesis regulation" Nippon Nogei Kagaku Kaishi, 72(12):1427-1437. 1998.

* cited by examiner

Primary Examiner — Daniel E Kolker
Assistant Examiner — Aditi Dutt
(74) Attorney, Agent, or Firm — Browdy and Neimark, PLLC

(57) ABSTRACT

A pharmaceutical for prevention and treatment of demyelination-associated neural function impairing diseases contains erythropoietin as an active ingredient, and protectively act on the survival of oligodendrocytes, which form a myelin sheath, in cerebrovascular dementia typified by multiple sclerosis and Binswanger disease, diseases involving demyelination. The pharmaceutical and method also promote maturation of undifferentiated oligodendrocytes present in the brain, activating remyelination. Through these mechanisms, the pharmaceutical and method can prevent and treat demyelination-associated neural function impairing diseases.

4 Claims, 7 Drawing Sheets

PHARMACEUTICAL FOR PREVENTION AND TREATMENT OF DEMYELINATING DISEASE

TECHNICAL FIELD

This invention relates to a pharmaceutical for prevention and treatment of demyelinating neural function disorders/diseases, especially, demyelinating cerebral function disorders/diseases, the pharmaceutical containing erythropoietin (EPO) as an active ingredient.

BACKGROUND ART

In recent years, progresses in diagnostic imaging techniques, such as MRI, have provided various findings. Based on these findings, it has been pointed out that a clear correspondence is not necessarily present between the frequent occurrence of cerebral infarction and dementia, and that Binswanger type cerebral infarction and leuko-ariosis correspond closely with symptoms of dementia. Furthermore, clinical investigations in our country have resulted in reports of many cases in which microvascular lesions without apoplectic stroke progress, leading to dementia (Akiguchi et al., 1995). The reports have indicated that not only in Binswanger type cerebral infarction, but also in the brains of elderly people, removal of the white matter, compared with the gray matter, is marked, and the loss of myelins, in particular, is severe. These reports suggest the possibility that many of diseases, generally categorized as cerebrovascular dementia, may be dementia due to demyelination. Myelin is a marrow sheath formed by the plasma membrane of oligodendrocytes (oligodendroglia cells) surrounding the axon. Because of demyelination, which primarily impairs this myelin sheath, the accuracy and the transmission speed of impulses propagated through the axons decline. This decline is presumed to cause higher function disorder, such as amnesia, or dyskinesia. As demyelination progresses, the nerve cells themselves degenerate and fall off. Thus, it is important to activate oligodendrocytes, which form the myelin sheath and support the nerve cells, in order to maintain the function of the nerve cells. Conventional therapies, which activate only nerve cells, cannot be expected to restore the function impaired by demyelinating disease.

Such demyelinating diseases showing dementia are becoming serious problems at the present time when society is rapidly aging. Development is hastily under way for therapeutic pharmaceuticals which are intended to prevent and treat these diseases and which act on oligodendrocytes by mechanisms different from the conventional therapies. The object of the present invention is, therefore, to provide a preventive and therapeutic pharmaceutical effective for the prevention and treatment of various diseases associated with demyelination.

DISCLOSURE OF THE INVENTION

The present inventors developed a method for culturing immature oligodendrocytes whose differentiation stages are uniform (Sakurai et al., 1998). They conducted in-depth studies on factors, which promote the maturation of oligodendrocytes, using as indicators the occurrence of myelin basic protein (MBP) specifically emerging upon maturation of oligodendrocytes, and the shapes and the number of processes or projections. As a result, they found that erythropoietin, a hematopoietic factor, promotes the occurrence of MBP directly or via astrocytes (astroglia), and has the action of maturing oligodendrocytes. Based on this finding, they have accomplished the present invention.

The object of the present invention is to provide a preventive and therapeutic pharmaceutical effective for the prevention and treatment of various diseases associated with demyelination. It has been reported in Cuprizone model (Ludwin 1980; Johnson & Ludwin, 1981), by experiments using chronic EAE models (Raine et al., 1988), and by studies on MS patient brains (Harrison, 1983; Prineas, 1975, 1978) that if demyelination occurs, the myelin sheath is repaired by remyelination. It is being generally accepted that once formed, myelin does not exist unchanged, but its destruction and remyelination take place. Actually, even in adults, undifferentiated (progenitor) cells of immature oligodendrocytes are confirmed not only in the subventricular zone, but also in the white matter region of the cerebral cortex (Gensert & Goldman, 1996). Thus, it is highly likely that myelination is taken charge of by neogenesis-migration-maturation of these undifferentiated oligodendrocytes under dynamic balance between destruction and formation (Gensert & Goldman, 1997; Roy et al., 1999).

The expression of EPO and EPO-R on the mRNA level was investigated by the RT-PCR method using nervous cells (oligodendrocytes, astrocytes and neurons) primarily cultured from the rat fetus brain and kidney and liver tissues isolated from adult rats. The expression of EPO-R was observed in all cells and tissues used, and the intense expression of EPO comparable to that in the kidney was observed in the oligodendrocytes. β-actin was used as a control.

FIGS. 2(a) to 2(c) are photographs showing the expression of EPO-R in oligodendrocyte cells. O4-positive oligodendrocytes (b) showed the expression of EPO-R in the entire region of the cell body and processes (c). The photograph (a) is a phase contrast photograph.

Figure 3:
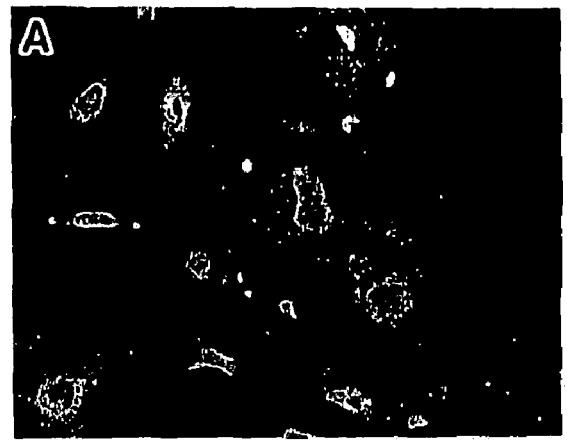
Figure 3:
Figure 3:

FIGS. 3A to 3C are photographs showing the expression of EPO-R in astrocyte cells. In GFAP-positive astrocytes (B), the expression of EPO-R was observed in particulate form widely on the cell surface (A), except the nucleus. The photograph C is a phase contrast photograph.

Figure 4:
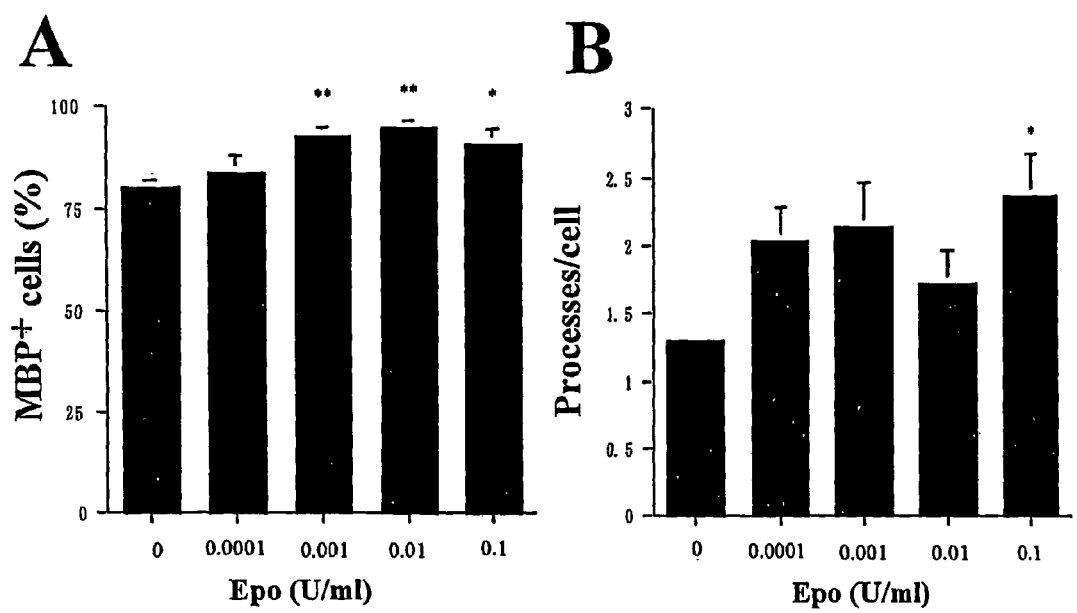

FIGS. 4A and 4B are graphs showing the effect of EPO on the percentage of MBP-positive oligodendrocyte cells (A), and changes in the average number of processes per cell by EPO (B).

After treatment with EPO in various concentrations (0.0001 to 0.1 U/ml) for 3 days, photographs were taken with a fluorescence microscope, and then the percentages of anti-MBP antibody-positive cells and the numbers of processes per cell were measured. The addition of EPO was found to increase the positiveness for MBP and the number of processes. The numerical values were expressed as means±standard errors, and the values were obtained from six independent observations. Statistically significant differences were tested by Dunnett's multiple comparison (*: $p<0.05$, **: $p<0.01$).

Figure 5:
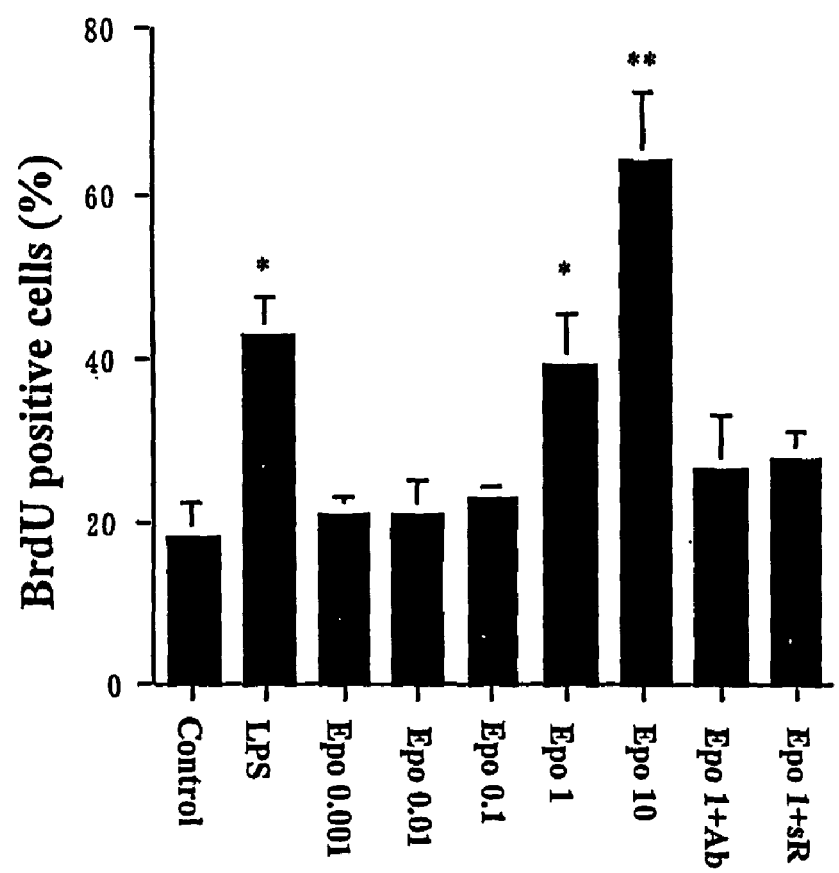

FIG. 5 is a graph showing the action of EPO on the BrdU uptake of astrocytes.

BrdU (20 μM) and the drug were added to the cells, and the cells were fixed 24 hours later. Then, the cells were immunostained with anti-BrdU antibodies and anti-GFAP antibodies, and the percentage of the number of the BrdU-positive cells was measured. The addition of LPS (20 μg/ml) and the addition of EPO were observed to promote the uptake of BrdU dose-dependently. The numerical values were expressed as means±standard errors obtained from three to four independent observations. Statistically significant differences were tested by Dunnett's multiple comparison (*: $p<0.05$, **: $p<0.01$).

Figure 6:
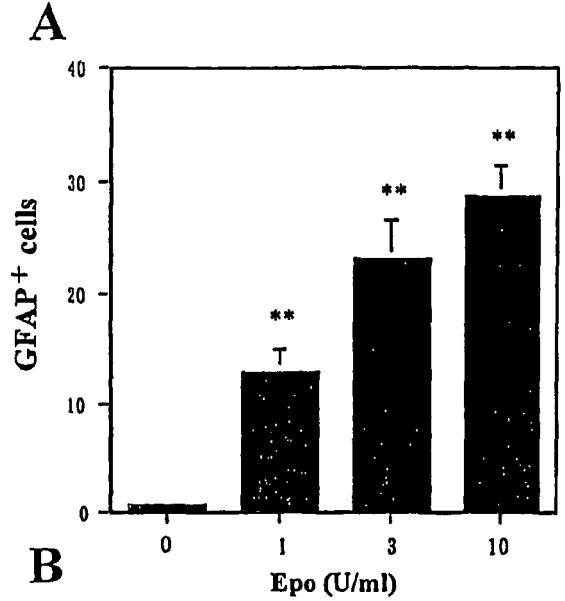
Figure 6:
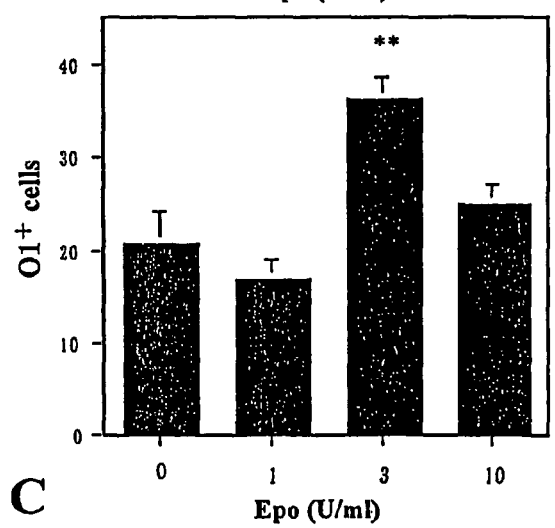
Figure 6:
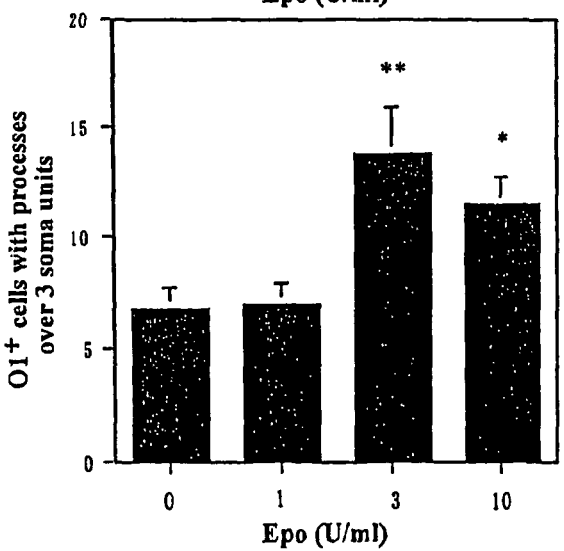

FIGS. 6A to 6C are graphs showing the effect of high concentration EPO on the increase of the number of coexistent astrocytes in a culture system of oligodendrocytes.

When EPO in high concentrations (1, 3, 10 U/ml) was added to the culture system, the dose-dependent increase of the number of coexisting GFAP-positive astrocytes was observed after the addition of 1 U/ml or more of EPO (A). Also, the increase in the number of viable oligodendrocytes (O1-positive) (B), and the promotion of maturation (growth of processes) (C) were observed. The numerical values were expressed as means±standard errors obtained from four to six independent observations. Statistically significant differences were tested by Dunnett's multiple comparison (*: $p<0.05$, **: $p<0.01$).

Figure 7:
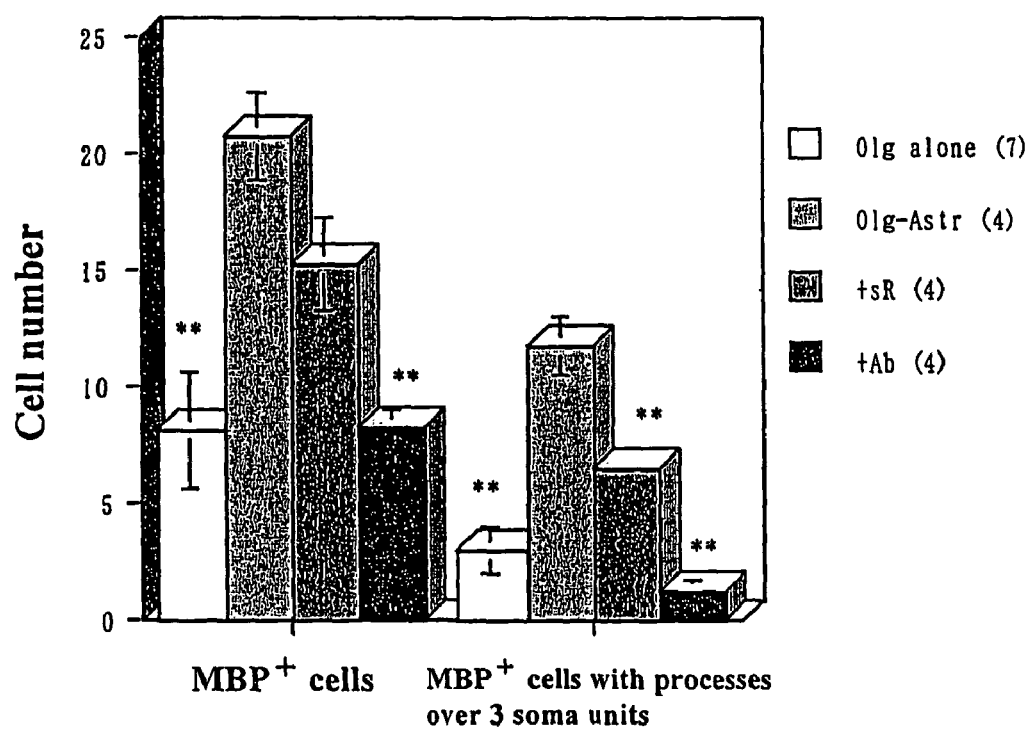

FIG. 7 is a graph showing the effects of the addition of soluble EPO-R and anti-EPO antibodies on the promotion of maturation of oligodendrocytes in an astrocyte/oligodendrocyte co-culture system.

Oligodendrocytes were cultured on a feeder layer of astrocytes. After cell adhesion, soluble EPO-R or anti-EPO antibodies were added. Three days later, immunostaining with anti-MBP antibodies was performed to calculate the proportion of MBP-positive cells and the proportion of MBP-positive cells forming three or more processes per cell body. The numerical values were expressed as means±standard errors obtained from four to seven independent observations. Statistically significant differences were tested by Dunnett's multiple comparison (*: $p<0.05$, **: $p<0.01$).

MODE FOR CARRYING OUT THE INVENTION

The present invention provides an epoch-making preventive and therapeutic pharmaceutical and an epoch-making preventive and therapeutic method targeting demyelinating diseases. The pharmaceutical and the method, as contrasted with conventional therapies using drugs targeted only at nerve cells, make erythropoietin act on oligodendrocytes directly and/or indirectly, via astrocytes, to prevent demyelination, thereby maturing undifferentiated oligodendrocytes. Thus, the pharmaceutical and the method can be expected to promote remyelination.

Demyelinating diseases in the present invention refer, in a broad sense, to a group of diseases in which the myelin sheath is primarily impaired. Actually, the demyelinating diseases are defined as a group of diseases mainly involving inflammatory myelin sheath lesions of unknown origin, with the exception of myelination deficiency diseases, such as leukodystrophy, and diseases due to obvious causes. Multiple sclerosis (MS) is a typical disease among demyelinating diseases, and pathologically, it is characterized by changes, mainly, inflammatory demyelination, and gliosis. Since its etiology is unknown, its diagnosis is made based on its clinical features, i.e., spatial multiplicity and multiplicity over time of central nervous system lesions. Furthermore, acute disseminated encephalomyelitis (ADEM), inflammatory diffuse sclerosis, and acute and subacute necrotizing hemorrhagic encephalomyelitis are included in demyelinating diseases.

In peripheral nervous tissues, the myelin sheath relies on Schwann's cells, and if they are impaired, peripheral demyelinating disease is caused. However, central demyelinating diseases will be mainly described in the present invention.

Erythropoietin (EPO), the active ingredient used in the present invention, includes, for example, naturally occurring human EPO obtained by extraction from the human urine of patients with aplastic anemia (Japanese Patent Publication No. 1989-38800), and products manufactured by genetic recombination technologies in which messenger RNA (mRNA) corresponding to the amino acid sequence of human EPO is collected, recombinant DNA is prepared with the use of the mRNA, and then the recombinant DNA is used for production by suitable hosts (e.g., microbes such as *Escherichia coli*, yeasts, cell strains of plants, and cell strains of animals, such as COS cells, Chinese hamster ovary cells (CHO), and mouse C-127 cells) [e.g., Japanese Patent Publication No. 1989-44317, Kenneth Jacobs et al., Nature, 313, 806-810 (1985)].

The EPO usable in the present invention may be those of the above origins, and their modification products. Examples of the EPO modification products are the modification products described in Japanese Unexamined Patent Publication No. 1991-151399. The above EPO modification products include those in which Asn of the peptide chains of the original glycoprotein varies to Gln, and the number of the N-linked sugar chains bonded is varied. Examples of those involving amino acid variations are described in Japanese Unexamined Patent Publication No. 1990-59599 and Japanese Unexamined Patent Publication No. 1991-72855. That is, the EPO modification products may have any number of amino acid variations, deletions or additions, unless they lose the action of EPO on the EPO receptor.

For the preparations of the present invention containing EPO as the active ingredient, suspending agents, solution adjuvants, stabilizers, tonicity agents, preservatives, and adsorption inhibitors may be added, where necessary, depending on their mode of administration and their dosage forms. Examples of the suspending agents include methylcellulose, polysorbate 80, hydroxyethylcellulose, acacia, tragacanth powder, sodium carboxymethylcellulose, and polyoxyethylene sorbitan monolaurate. Examples of the solution adjuvants are polyoxyethylene hydrogenated castor oil, polysorbate 80, nicotinamide, polyoxyethylene sorbitan monolaurate, macrogol, and castor oil fatty acid ethyl ester. Examples of the stabilizers are human serum albumin, dextran 40, methylcellulose, gelatin, sodium sulfite, and sodium metasulfite. Examples of the tonicity agents are D-mannitol and sorbitol. Examples of the preservatives are methyl parahydroxybenzoate, ethyl parahydroxybenzoate, sorbic acid, phenol, cresol, and chlorocresol. Examples of the adsorption inhibitors are human serum albumin, lecithin, dextran, ethylene oxide-propylene oxide copolymer, hydroxypropylcellulose, methylcellulose, polyoxyethylene hydrogenated castor oil, and polyethylene glycol.

Also available is a stable EPO pharmaceutical solution according to the present invention which contains EPO as an active ingredient and which is free from human serum albumin or purified gelatin, if a certain type of amino acid is added as a stabilizer. This stable EPO pharmaceutical solution is described in Japanese Unexamined Patent Publication No. 1998-182481. It is to be understood that the descriptions in this publication are included as part of the specification of the present application.

The amino acids added as the stabilizers in the EPO pharmaceutical solution include free amino acids, and their salts such as sodium salts, potassium salts, and hydrochlorides. The pharmaceutical solution of the present invention can incorporate one or more of these amino acids in combination. The preferred amino acids are leucine, tryptophan, serine, glutamic acid, arginine, histidine, and lysine in D-, L- and DL-forms, and their salts. More preferable are L-leucine, L-tryptophan, L-glutamic acid, L-arginine, L-histidine and L-lysine, and their salts. Particularly preferred are L-arginine, L-histidine and L-lysine, and their salts. The most preferred amino acids are L-histidine and its salts. Details of the method for preparing the EPO pharmaceutical solution are as described in the above publication.

The doses of these EPO's in the preventive and therapeutic pharmaceuticals, the object of the present invention, can be determined, as desired, in consideration of the targeted diseases and their disease states. Usually, the dose is 0.1 to 500 µg, preferably 5 to 100 µg, per adult.

Experimental Examples for confirming the efficacy of the present invention will be offered below.

[1] Preparation of Primary Culture Cells 1-1: Culture of Oligodendrocytes

Culture of oligodendrocyte cells in the immature stage was performed using 18-day fetal rats. The cerebrum was enzymatically dispersed in a dispase II (0.3 ng/ml, Boehringer Mannheim)+0.05% DNAse (Boehringer Mannheim) solution [Dulbecco-modified Eagle's medium (DMEM)]. The resulting dispersed cells were washed with DMEM, then passed through a nylon mesh with a pore size of 70 µm (Becton Dickinson, #2350), seeded on a poly-L-lysine(ICN)-coated culture dish ($1.4 \times 10^7$ cells/60 cm), and cultured for 7 days in an incubator (phase I).

Then, the cells were passaged in 0.25% trypsin/phosphate buffered saline (PBS), and centrifuged for 10 minutes ($4°$ C., 1,000 rpm). After the supernatant was discarded, the cells were suspended in DMEM/10% fetal bovine serum (FBS) and seeded at a rate of $2 \times 10^6$ cells/dish. Two days later, the medium was replaced by a serum-free medium [DMEM+ glucose (5 mg/ml), insulin (5 µg/ml), sodium selenate (40 ng/ml), transferrin (100 µg/ml), progestron (0.06 ng/ml), putrescine (16 µg/ml), thyroxine (40 ng/ml), triiodothyronine (30 ng/ml), bFGF (2 ng/ml)], and the cells were cultured for 5 more days (phase II). This process of phase II, involving passage with trypsin treatment, followed by culture for 7 days, was repeated 3 times, and the resulting cells were used in experiments as immature oligodendrocytes.

1-2: Culture of Astrocytes

The cerebrum of neonatal rats was treated with a 0.25% trypsin solution for 10 minute at $37°$ C., and a DMEM/5% calf serum (CS)+0.2% glucose medium was added. This culture medium was passed through a No. 40 stainless steel mesh with a pore size of 320 µm, and recovered onto a culture dish. This cell suspension was centrifuged for 5 minutes at 800 rpm, and the supernatant was removed. The sediment was resuspended in the above culture medium by pipetting, and centrifuged again. The centrifugation-resuspension cycle was repeated 3 times, and finally the cells were seeded in a medium (DMEM/5% CS+0.4% glucose, 0.05% $NaHCO_3$, 292 µg/ml glutamine, 100 µg/ml kanamycin) to a cell count of $10^6$ cells/ml on a tissue culture dish. After culture was performed for 2 to 4 weeks in a 5% $CO_2$ incubator, the confluent cells were preserved in frozen state at a cell banker. These frozen cells were awakened, and cultured for about 2 weeks for use in experiments.

1-3: Co-Culture of Oligodendrocytes and Astrocytes

The oligodendrocytes, which had been prepared by the method of 1-1, were seeded on a feeder layer of the astrocytes that had been cultured by the method of 1-2 until becoming nearly confluent.

1-4: Culture of Neurons

A fetal brain was removed from a rat at 18 days in gestation, and a cerebral neocortex tissue including the hippocampus was isolated in an ice-cooled Hanks' balanced salt solution (HBSS) under a microscope. The isolated tissue was mashed on a No. 40 mesh with a pore size of 320 µm, and washed with a DMEM/10% FBS-0.05% DNase/HBSS (1:1) mixed solution, whereby it was passed through the mesh. Then, pipetting was performed 10 to 15 times using a Pasteur pipette with a round-burned front end, whereafter the sample was passed through a No. 100 stainless steel mesh, and then recovered into a 15 ml centrifuge tube, where it was centrifuged (800 rpm, $4°$ C., 10 min). The supernatant was discarded, and the residue was resuspended in the above-mentioned mixed solution. The suspension was subjected to repeated pipetting and centrifugation. Then, the cells were suspended in Neurobasal medium (Gibco)/B27 supplement (Gibco):D-MEM/10% FBS (1:1) medium, and passed through a lens paper. Then, the number of the cells was counted, and the cells were seeded on a polylysine-coated dish, and cultured in a 5% $CO_2$ incubator. Twenty-four hours later, the medium was replaced by Neurobasal medium/B27 supplement medium. Then, the cells were cultured for 5 to 6 days and used in experiments.

[2] Study of Expression of EPO Receptor by RT-PCR

The various cells (oligodendrocytes, astrocytes, neurons) cultured by the above-described methods, and the liver and kidney isolated from young mature rats were treated with Trizol Solution (Gibco), and total RNA was extracted in accordance with instructions of the attached manual. A reverse transcription reaction of the extracted total RNA (ca. 500 ng) was performed for 30 minutes at $42°$ C., 5 minutes at $99°$ C., and 5 minutes at $5°$ C. using an RNA/PCR kit (Takara), to synthesize cDNA (10 µl). The following primer pairs specific for the synthetic DNA were added, and the DNA was amplified using the above PCR kit. Beta-actin (β-actin) was used as a control.

| RT-PCR analysis primers | |
|---|---|
| rat EPO: | 5'-ACCACTCCCAACCCTCATCAA (forward) SEQ ID NO: 1 |
| | 5'-CGTCCAGCACCCCGTAAATAG (reverse) SEQ ID NO: 2 |
| | product size: 325 bp |
| rat EPO-R: | 5'-TGGATGAATGGTTGCTAC (forward) SEQ ID NO: 3 |
| | 5'-TTTGAAGCCAAGTCAGAG (reverse) SEQ ID NO: 4 |
| | product size: 127 bp |
| rat β-actin: | 5'-CGTAAAGACCTCTATGCCAA (forward) SEQ ID NO: 5 |
| | 5'-AGCCATGCCAAATGTCTCAT (reverse) SEQ ID NO: 6 |
| | product size: 349 bp |

[3] Study by Immunocytochemistry

The cells, which had been cultured on a microcover glass, were used in the analysis of immunocytochemistry.

3-1: Study of Expression of EPO-R Using Anti-EPO Receptor (R) Antibodies

The cells were fixed for 15 minutes in a periodate-lysine-paraformaldehyde (PLP) solution, and blocked with a blocking buffer (BB,PBS/10% Horse serum) for 30 minutes. Then, the cells were treated overnight or for 1 hour with anti-O4 monoclonal antibodies (diluted 1:40) in the case of oligodendrocytes, or with anti-GFAP polyclonal antibodies (diluted 1:2000, Dako) in the case of astrocytes. Then, the cells were treated for 1 hour with anti-mouse IgM (FITC labeled, diluted 1:200) [or with anti-rabbit IgG antibodies (FITC labeled, diluted 1:200) in the case of astrocytes]. Then, the cells were fixed for 15 minutes in a 2% paraformaldehyde (PFA) solution, treated with anti-EPO-R antibodies (diluted 1:100, Upstate biotechnology, No. 06-406) for 1 hour, and treated with a 1:200 diluted solution of anti-rabbit IgG (rhodamine labeled) for 1 hour, followed by mounting. Photographs of the cells were taken with a fluorescence microscope.

3-2: Percentage of Cells Expressing MBP

The MBP-expressed cells were evaluated by an immunohistochemical method using anti-MBP antibodies. That is, the aforementioned cells (oligodendrocytes cultured alone, and oligodendrocytes and astrocytes cultured concomitantly) 3 days after addition of the drug were fixed in a 2% PFA solution for 30 minutes, treated with a 0.1% Triton X-100/PBS solution for 10 minutes, and blocked with BB for 30 minutes. Then, the cells were treated for 1 hour with anti-MBP polyclonal antibodies (diluted 1:10, Nichirei), then treated with a 1:200 diluted solution of anti-rabbit IgG (FITC labeled) for 1 hour, and mounted. Photographs of the cells were taken with a fluorescence microscope, and the percentages and the numbers of processes of the MBP-positive cells were calculated.

[4] Experiments on Uptake of BrdU

The respective cells cultured by the aforesaid methods of 1-1 and 1-2 were forced to take up BrdU (final concentration 20 μM) for 48 hours in the case of oligodendrocytes or 24 hours in the case of astrocytes. Then, the cells were fixed in 70% ethanol at −20° C. for 10 minutes, treated with 2N-HCL for 10 minutes and $0.1M-Na_2B_4O_7$ for 5 minutes, and blocked with BB for 30 minutes. Then, anti-BrdU monoclonal antibodies (Sigma B2531, diluted 1:1000), which had been diluted 1:500, were added for 1 hour, whereafter the cells were treated with anti-mouse IgG antibodies (FITC labeled) for 1 hour. Then, the BrdU-positive cells were measured under a fluorescence microscope.

[5] Preparation of EPO

When added to the culture medium, human erythropoietin (trade name: Epogin) was adjusted to different concentrations by dilution with a PBS/10% FBS solution to become 1:100 dilutions. The PBS/10% FBS solution was used as the control.

<Results of Experiments>

Figure 1:
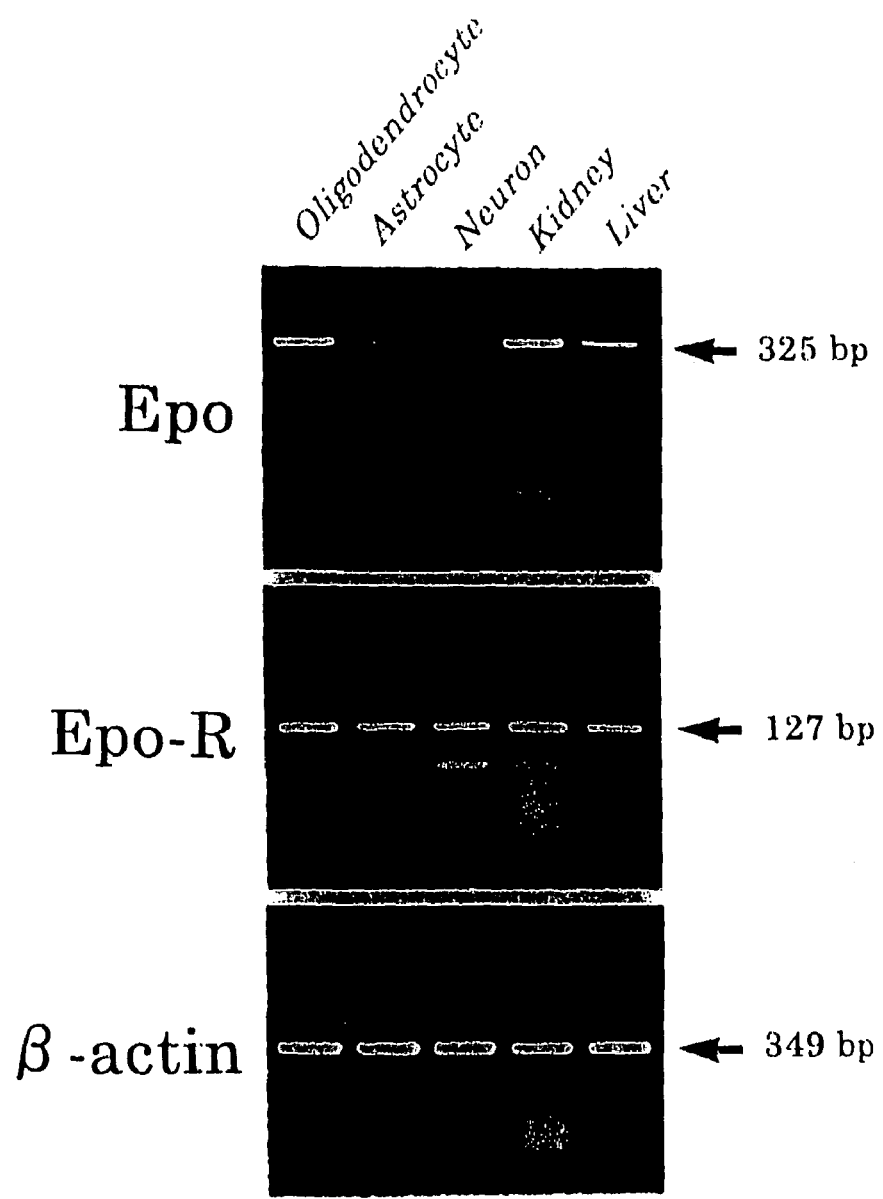
FIG. 1 is a photograph showing the expression of EPO and EPO-R on the mRNA level in cultured nervous cells and isolated kidney and liver tissues.
Figure 2:

When the expression of EPO-R and EPO was investigated by PCR, the expression of EPO was observed in the order of decreasing intensity, kidney>oligodendrocytes>liver>astrocytes, and a very thin band was found in neurons (FIG. 1). EPO-R showed somewhat strong expression in the kidney and oligodendrocytes, but the expression was on nearly the same level among the different tissues (FIG. 1). Immunofluorescence staining was performed in order to confirm the expression of EPO-R on the protein level. The expression of EPO-R was observed in the O4-positive oligodendrocytes throughout the cell body and the processes (FIG. 2). In the GFAP-positive astrocytes as well, the presence of EPO-R was confirmed in particulate form in nearly all regions on the cell surface, except the nucleus (FIGS. 3A to 3C).

Based on these results, oligodendrocytes and astrocytes are presumed to be cells which express EPO-R on the mRNA and protein levels and respond to EPO. Thus, recombinant human EPO protein was added to a culture medium of cultured cells, and morphological changes and expression of MBP after 3 days were investigated to study the effect of EPO on the maturation of oligodendrocytes. As shown in FIGS. 4A and 4B, a tendency toward an increase in the percentage of the number of MBP-positive cells was observed in all of the treated groups (0.0001 to 0.1 U/ml) in comparison with the control, and significant increases were noted in the treatment groups receiving the concentrations of 0.001 U/ml or more (*: $p<0.05$, **: $p<0.01$, Dunnett's multiple comparison). The number of processes per cell body also increased similarly upon EPO treatment, and the increase following addition of 0.1 U/ml of EPO was significant compared with the control ($p<0.05$, Dunnett's multiple comparison).

In the astrocytes, marked uptake of BrdU was observed after addition of EPO in high concentrations (1 and 10 U/ml) (*:$p<0.05$, **: $p<0.01$). This action weakened, although not significantly, with the addition of anti-EPO antibodies having EPO-neutralizing activity, or soluble EPO receptors (FIG. 5). In agreement with this outcome, when EPO in high concentrations of 1 to 10 U/ml was added to the culture system of oligodendrocytes, significant increases in the number of GFAP-positive astrocytes that coexisted were observed dose-dependently, and viability and maturity (O1 expression, number of processes) of oligodendrocytes were accelerated (FIGS. 6A to 6C).

Next, study was conducted of the effects of anti-EPO antibodies and soluble EPO-R (sEPO-R) in an astrocyte-oligodendrocyte co-culture system. The present inventors have so far clarified that when oligodendrocytes are cultured on a feeder layer of astrocytes, thick processes are formed, and positiveness for MBP increases, thus showing promoted maturity (Sakurai et al., 1998). Anti-EPO antibodies having neutralizing activity or sEPO-R were added to this co-culture system, and the maturation of the oligodendrocytes was evaluated by stainability with anti-MBP antibodies and process formation (the number of cells having 3 or more processes per cell body). As clear from the results shown in FIG. 7, the number of MBP-positive cells markedly increased, and the promotion of process formation was also observed, when oligodendrocytes were co-cultured on astrocytes, as compared with when oligodendrocytes were cultured alone. On the other hand, the group receiving the addition of SEPO-R showed a tendency toward a decrease in the number of MBP-positive cells, and significant suppression of process formation, as compared with the control group ($p<0.01$, Dunnett's multiple comparison). Whereas the group receiving the anti-EPO antibodies showed significant decreases in both of the number of MBP-positive cells and the formation of processes ($p<0.01$, Dunnett's multiple comparison). These results suggest that EPO is involved, at least partly, in the maturation of oligodendrocytes by interaction with astrocytes.

The above-described outcomes suggest the possibility that although in vitro, EPO directly promotes the maturation of oligodendrocytes in the brain when its concentration is low (0.001 to 0.1 U/ml), while EPO acts on the maturation of oligodendrocytes through the activation of astrocytes when its concentration is high (>1 U/ml). Thus, the present invention is the first to show the action of EPO on oligodendrocytes, as contrasted with the hitherto reported effects of EPO on nerve cells, such as an activating effect on cholinergic nerve cells (Konishi et al., 1993; Tabira et al., 1995; Japanese Unexamined Patent Publication No. 1993-92928; Japanese Unexamined Patent Publication No. 1993-246885), neuroprotective effect on glutamate-induced neurotoxicity (Morishita et al., 1997), inhibitory effect on neuronal death due to cerebral ischemia (Sakanaka et al., 1998; Sadamoto et al., 1998; Bernaudin et al., 1999).

In recent years, demyelination has been pointed out not only in multiple sclerosis, but also in cerebrovascular dementia and Alzheimer disease. It is considered difficult for conventional medicines acting on nerve cells, if used alone, to take care of these diseases presenting with dementia. Nerve cells, which have already undergone demyelination, die in the meantime unless oligodendrocytes are present. However, it is becoming clear that myelin formation continues even in adults (after maturation), and progenitor cells of undifferentiated oligodendrocytes are born in the subventricular zone. These cells migrate to the white matter region of the cerebral cortex, where they become mature and carry out new myelin formation. Thus, it is suggested that the cycle of destruction and formation of myelin is present (Gensert & Goldman, 1996, 1997; Roy et al., 1999). The present invention aims to activate this cycle, thereby treating demyelinating diseases, which have not been curable only with conventional protective agents for nerve cells, by repair of myelins through maturation of oligodendrocytes. EPO is believed to be effective as a therapeutic agent for wide varieties of brain diseases involving demyelination.

Examples concerned with pharmaceutical products will be offered below.

Example 1

| | |
|---|---|
| Erythropoietin | 8 μg |
| Total amount with distilled water for injection | 2 ml |

A solution of the above composition was aseptically prepared, dispensed into a vial, and sealed up.

Example 2

| | |
|---|---|
| Erythropoietin | 8 μg |
| Total amount with distilled water for injection | 2 ml |

A solution of the above composition was aseptically prepared, dispensed into a vial, freeze-dried, and sealed up.

Example 3

| | |
|---|---|
| Erythropoietin | 16 μg |
| Total amount with distilled water for injection | 2 ml |

A solution of the above composition was aseptically prepared, dispensed into a vial, and sealed up.

Example 4

| | |
|---|---|
| Erythropoietin | 16 μg |
| Total amount with distilled water for injection | 2 ml |

A solution of the above composition was aseptically prepared, dispensed into a vial, freeze-dried, and sealed up.

Example 5

| | |
|---|---|
| Erythropoietin | 8 μg |
| Human serum albumin | 5 mg |
| Total amount with distilled water for injection | 2 ml |

A solution of the above composition was aseptically prepared, dispensed into a vial, and sealed up.

Example 6

| | |
|---|---|
| Erythropoietin | 8 μg |
| Human serum albumin | 5 mg |
| Total amount with distilled water for injection | 2 ml |

A solution of the above composition was aseptically prepared, dispensed into a vial, freeze-dried, and sealed up.

Example 7

| | |
|---|---|
| Erythropoietin | 16 μg |
| Human serum albumin | 5 mg |
| Total amount with distilled water for injection | 2 ml |

A solution of the above composition was aseptically prepared, dispensed into a vial, and sealed up.

Example 8

| | |
|---|---|
| Erythropoietin | 16 μg |
| Gelatin | 5 mg |
| Total amount with distilled water for injection | 2 ml |

A solution of the above composition was aseptically prepared, dispensed into a vial, freeze-dried, and sealed up.

Examples 9 to 12

Instead of the human serum albumin in Examples 5 to 8, 5 mg of dextran 40 was used, and the ingredients were treated in the same manner as in Examples 5 to 8 to prepare injections.

Example 13

In 100 ml of distilled water for injection, 5 g of D-mannitol, 1 mg of erythropoietin, and 100 mg of human serum albumin were aseptically dissolved to prepare an aqueous solution.

The aqueous solution was dispensed into vials in an amount of 1 ml per vial, freeze-dried, and sealed up.

Example 14

A solution adjusted to pH 6.0 with a 10 mM phosphate buffer solution (Wako Pure Chemical) and containing the following ingredients in 1 ml of the prepared solution

| | |
|---|---|
| EPO | 1,500 IU |
| Nonionic surface active agent (polysorbate 80: Nikko Chemical) | 0.05 mg |
| Sodium chloride | 8.5 mg |
| L-arginine hydrochloride (Sigma) | 10 mg | was charged in an amount of 1 ml into a 5 ml glass vial, stoppered, and sealed up for use as a pharmaceutical solution.

Example 15

A pharmaceutical solution was prepared by the same procedure as in Example 14 using the solution containing the following ingredients in 1 ml of the prepared solution:

| | |
|---|---|
| EPO | 1,500 IU |
| Nonionic surface active agent (polysorbate 80: Nikko Chemical) | 0.05 mg |
| Sodium chloride | 8.5 mg |
| L-histidine hydrochloride (Sigma) | 10 mg |

Example 16

A pharmaceutical solution was prepared by the same procedure as in Example 14 using the solution containing the following ingredients in 1 ml of the prepared solution:

| | |
|---|---|
| EPO | 1,500 IU |
| Nonionic surface active agent (polysorbate 80: Nikko Chemical) | 0.05 mg |
| Sodium chloride | 8.5 mg |
| L-lysine hydrochloride (Sigma) | 10 mg |

INDUSTRIAL APPLICABILITY

The pharmaceutical product containing EPO as an active ingredient according to the present invention is an epoch-making preventive and therapeutic pharmaceutical which, as contrasted with conventional therapies using drugs targeted only at nerve cells, makes erythropoietin act on oligodendrocytes directly and indirectly, via astrocytes, to prevent demyelination, thereby maturing undifferentiated oligodendrocytes, leading to promotion of remyelination.

CITED REFERENCES

Akiguchi I, Tomimoto H, Suenaga T (1995): Pathology of Binswanger type cerebrovascular dementia, Clinic All-round, 44, 834-839

Bernaudin M, Marti H H, Roussel S, Divoux D, Nouvelot A, MacKenzie E T, Petit E (1999): A potential role for erythropoietin in focal permanent cerebral ischemia in mice, J Cereb. *Blood flow Metab.*, 19, 643-651

Genser J M, Goldman J E (1996): In vivo characterization of endogenous proliferating cells in adult rat subcortical white matter, *Glia* 17, 39-51

Genser J M, Goldman J E (1997): Endogenous progenitors remyelinate demyelinated axons in the adult CNS, *Neuron* 19, 197-203

Harrison B M (1983): Remyelination in the central nervous system. In: *Multiple Sclerosis*. J F Halpike, C M Adams, W W Tourtelotte eds. Baltimore, Williams & Wilkins, pp. 461-478

Johnson E S, Ludwin S K (1981): The demonstration of recurrent demyelination and remyelination of axons in the central nervous system, *Acta Neuropatholo.* (Berl.), 53, 93-98

Konishi Y, Chui D-H, Hirose H, Kunishita T, Tabira T (1993): Trophic effect of erythropoietin and other hematopoietic factors on central cholinergic neurons in vitro and in vivo, *Brain Res.*, 606, 29-35

Ludwin S K (1989): Chronic demyelination inhibits remyelination in the central nervous system: An analysis of contributing factors, *Lab. Invest.* 43, 382-387

Morishita E, Masuda S, Nagao M, Yasuda Y, Sasaki R (1997): Erythropoietin receptor is expressed in rat hippocampal and cerebral cortical neurons, and erythropoietin prevents in vitro glutamate-induced neuronal death, *Neuroscience*, 76, 105-116

Prineas J W (1975): Pathology of the early lesion in multiple sclerosis, *Hum. Pathol.* 6, 531-554

Prineas J W (1985): The neuropathology of multiple sclerosis. In: *Handbook of Clinical Neurology*, Vol. 3 (47): Demyelinating Diseases. J C Koetsier, P J Vinken, G W Bruyn, H L Klawans eds. Amsterdam, Elsevier Science Publishers, pp. 213-257

Raine C S, Hintzen R, Traugott U, Moore G R (1988): Oligodendrocyte proliferation and enhanced CNS remyelination after therapeutic manipulation of chronic relapsing EAE. *Ann. N.Y. Acad. Sci.* 540:712-714

Roy N S, Wang S, Harrison-Restelli C, Benraiss A, Fraser R A R, Gravel M, Braun P E, Goldman S A (1999): Identification, isolation, and promoter-defined separation of mitotic oligodendrocyte progenitor cells from the adult human subcortical white matter, *J. Neurosci.* 22, 9986-9995

Sadamoto Y, Igase K, Sakanaka M, Sato K, Otsuka H, Sakai S, Masuda S, Sasaki R (1988): Erythropoietin prevents place navigation disability and cortical infarction in rats with permanent occlusion of the middle cerebral artery, *Biochem. Biophys. Res. Comm.*, 253, 26-32

Sakanaka M, Wen T-C, Matsuda S, Masuda S, Morishita E, Nagao M, Sasaki R (1998): In vivo evidence that erythropoietin protects neurons from ischemic damage, *Proc. Natl. Acad. Sci. USA*, 95, 4635-4540

Sakurai Y, Nishimura D, Yoshimura K, Tsuruo Y, Seiwa C, Asou H (1998): Differentiation of oligodendrocyte occurs in contact with astrocyte, *J. Neurosci. Res.* 52, 17-26

Tabira T, Konishi Y, Gallyas F. (1995): Neurotrophic effect of hematopoietic cytokines on cholinergic and other neurons in vitro, *Int. J. Devl. Neurosci.*, 13, 241-252

Japanese Unexamined Patent Publication No. 1993-92928

Japanese Unexamined Patent Publication No. 1993-246885.

The invention claimed is:

1. A method of promoting maturation of oligodendrocyte cells, said method comprising:
   treating oligodendrocyte progenitor cells ex vivo, with an effective amount of erythropoietin,
   wherein the erythropoietin is selected from naturally occurring human erythropoietin or recombinant human erythropoietin.

2. The method of claim 1, wherein the oligodendrocyte progenitor cells are co-cultured with astrocytes.

3. A method of increasing oligodendrocyte progenitor cell proliferation, said method comprising:
   treating oligodendrocyte progenitor cells ex vivo, with an effective amount of erythropoietin,
   wherein the erythropoietin is selected from naturally occurring human erythropoietin or recombinant human erythropoietin.

4. The method of claim 3, wherein the oligodendrocyte progenitor cells are co-cultured with astrocytes.

* * * * *

SEQUENCE LISTING

<160> NUMBER OF SEQ ID NOS: 6

<210> SEQ ID NO 1
<211> LENGTH: 21
<212> TYPE: DNA
<213> ORGANISM: Artificial
<220> FEATURE:
<223> OTHER INFORMATION: synthetic

<400> SEQUENCE: 1
accactccca accctcatca a                                              21

<210> SEQ ID NO 2
<211> LENGTH: 21
<212> TYPE: DNA
<213> ORGANISM: Artificial
<220> FEATURE:
<223> OTHER INFORMATION: synthetic

<400> SEQUENCE: 2
cgtccagcac cccgtaaata g                                              21

<210> SEQ ID NO 3
<211> LENGTH: 18
<212> TYPE: DNA
<213> ORGANISM: Artificial
<220> FEATURE:
<223> OTHER INFORMATION: synthetic

<400> SEQUENCE: 3
tggatgaatg gttgctac                                                  18

<210> SEQ ID NO 4
<211> LENGTH: 18
<212> TYPE: DNA
<213> ORGANISM: Artificial
<220> FEATURE:
<223> OTHER INFORMATION: synthetic

<400> SEQUENCE: 4
tttgaagcca agtcagag                                                  18

<210> SEQ ID NO 5
<211> LENGTH: 20
<212> TYPE: DNA
<213> ORGANISM: Artificial
<220> FEATURE:
<223> OTHER INFORMATION: synthetic

<400> SEQUENCE: 5
cgtaaagacc tctatgccaa                                                20

<210> SEQ ID NO 6
<211> LENGTH: 20
<212> TYPE: DNA
<213> ORGANISM: Artificial
<220> FEATURE:
<223> OTHER INFORMATION: synthetic

<400> SEQUENCE: 6
agccatgcca aatgtctcat                                                20